US00PP32599P2

(12) United States Plant Patent
Bak et al.

(10) Patent No.: US PP32,599 P2
(45) Date of Patent: Dec. 8, 2020

(54) ***VRIESEA* PLANT NAMED 'FLARE'**

(50) Latin Name: *Vriesea hybrida*
Varietal Denomination: FLARE

(71) Applicant: Corn Bak B.V., Assendelft (NL)

(72) Inventors: Elly Bak, Rijsenhout (NL); Nicolaas D. M. Steur, Oude Niedorp (NL)

(73) Assignee: Corn Bak B.V. (NL)

( * ) Notice: Subject to any disclaimer, the term of this patent is extended or adjusted under 35 U.S.C. 154(b) by 0 days.

(21) Appl. No.: 16/602,602

(22) Filed: Nov. 4, 2019

(51) Int. Cl.
*A01H 5/02* (2018.01)
*A01H 6/22* (2018.01)

(52) U.S. Cl.
USPC ..... Plt./370
CPC ..... *A01H 6/228* (2018.05)

(58) Field of Classification Search
USPC ..... Plt./370
CPC ..... A01H 5/02
See application file for complete search history.

(56) References Cited

PUBLICATIONS https://www.bsnz.org/journals/2016/august-2016-journal; Aug. 2016; 3 pages.*

* cited by examiner

*Primary Examiner* — Kent L Bell
(74) *Attorney, Agent, or Firm* — Cassandra Bright

(57) ABSTRACT

A new and distinct *Vriesea* plant named 'FLARE' characterized as a funnel form rosette plant, measuring about 34 cm in height (when flowering) and 40 cm in diameter, producing compound, orange-red in color, bipinnate spike inflorescence, measuring about 25 cm in length and about 12 cm in width, and about 6 to 7 branches, and yellow-green foliage, measuring about 26 cm in length and about 3.5 cm in width.

1 Drawing Sheet

Latin name of the genus and species: *Vriesea hybrida.*
Variety denomination: 'FLARE'.

BACKGROUND OF THE INVENTION

The present invention relates to a new and distinct cultivar of *Vriesea* plant, botanically known as *Vriesea hybrida*, hereinafter referred to by the cultivar name 'FLARE'. The genus of *Vriesea* belongs to the Bromeliaceae family. The new *Vriesea* cultivar is a product of a planned breeding program conducted by the inventors, Elly Bak and Nico D. M. Steur, in Assendelft, The Netherlands. The objective of the breeding program is to develop a new *Vriesea* variety with good growing habit and attractive inflorescence.

The new *Vriesea* cultivar 'FLARE' originated from a cross-made in a controlled breeding program by the inventors in 1997 in Assendelft, The Netherlands. The seed parent is an unpatented *Vriesea* selection designated '930484'. The pollen parent is an unpatented *Vriesea* selection designated '930370'. 'FLARE' was discovered and selected by the inventors in 2002, as a single flowering plant within the progeny of the stated cross in a controlled environment in Assendelft, The Netherlands.

Asexual reproduction of the new cultivar 'FLARE' was first performed by tissue culture in 2014, in Assendelft, The Netherlands. The first 'FLARE' plants propagated through the use of tissue culture flowered in 2018, in Assendelft, The Netherlands, and have demonstrated that the combination of characteristics as herein disclosed for the new cultivar are firmly fixed and retained through successive generations of asexual reproduction. The new cultivar reproduces true-to-type.

SUMMARY OF THE INVENTION

The cultivar 'FLARE' has not been observed under all possible environmental conditions. The phenotype may vary somewhat with variations in environment such as temperature, day length, and light intensity, without, however, any variance in genotype.

BRIEF DESCRIPTION OF THE INVENTION

The following traits have been repeatedly observed and are determined to be the unique characteristics of 'FLARE'. These characteristics in combination distinguish 'FLARE' as a new and distinct *Vriesea* cultivar:

1. Funnel form rosette.
2. Compound, orange-red bipinnate spike inflorescence.
3. About 6-7 branches.
4. Yellow green foliage.

PARENT COMPARISON

Plants of the parents are no longer available to provide a botanical comparison with the new *Vriesea* cultivar 'FLARE'.

COMMERCIAL COMPARISON

'FLARE' is similar in most horticultural characteristics to the unpatented commercial variety *Vriesea* 'Shade', U.S. Plant patent application Ser. No. 16/602,006. However the new variety, 'FLARE' differs in the following:

1. The new variety is a smaller plant than this comparator.
2. This comparator has 3 bract-like branches below its main inflorescence, while the new variety does not.

BRIEF DESCRIPTION OF THE PHOTOGRAPH

The accompanying figure illustrates the overall appearance of the new *Vriesea* cultivar 'FLARE' showing the colors as true as is reasonably possible with colored reproductions of this type. Colors in the photograph may differ slightly from the color values cited in the detailed botanical description which accurately describes the color of 'FLARE'. The photograph shows a side perspective view of a typical potted flowering plant of 'FLARE' at about 18 months of age from potting.

DETAILED BOTANICAL DESCRIPTION

'FLARE' has not been observed under all possible environmental conditions. The phenotype of the new cultivar may vary with variations in environment such as temperature, light intensity, day length, fertilizers and humidity without any change in the genotype of the plant. The afore mentioned photograph, together with the following observations, measurements and values describe the new *Vriesea* cultivar as grown in a greenhouse in Assendelft, The Netherlands, under conditions which closely approximate those generally used in commercial practice. Plants of 'FLARE' were grown in a greenhouse with day temperatures ranging from 20° C. to 28° C. and night temperatures ranging from 18° C. to 23° C. No artificial lighting or photoperiodic treatments were conducted, but plants of 'FLARE' are forced into flowering. The following fertilizer is added when growing plants of 'FLARE': 1 part nitrogen, 0.6 parts phosphor, 2 parts Kalium and 0.1 parts magnesium. Color references are made to The Royal Horticultural Society Colour Chart (R.H.S.), 2007 except where general colors of ordinary significance are used. Color values were taken under daylight conditions in a greenhouse in Assendelft, The Netherlands. The age of the plants of 'FLARE' described is about 18 months from potting.

Botanical classification: *Vriesea hybrida* 'FLARE'.

PROPAGATION

Type of propagation typically used: Tissue culture.

PLANT

Shape: Funnel form rosette.
Height: Approximately: 34 cm.
Plant spread: Approximately: 40 cm.
Plant vigor: Good.
Flowering season: A fully grown plant can flower year-round, starting 15 weeks after induction of natural light or through flowering treatment.
Cold tolerance: Frost tender. Temperatures below 5° C. may damage plants.
Fragrance: None.
Root description: Densely branched, non-fibrous, non-fleshy, colored Greyed-orange; near RHS 165C.

FOLIAGE

Leaf:
- *Quantity*.—About 20.
- *Average length*.—About 26 cm.
- *Average width*.—About 3.5 cm.
- *Shape of blade*.—Broad and linear.
- *Apex*.—Abruptly acuminate.
- *Base*.—Strap-like around central axis.
- *Margin*.—Entire.
- *Texture of top surface*.—Smooth, glabrous.
- *Texture of bottom surface*.—Smooth, glabrous.
- *Color*.—Leaf color can vary depending on growing conditions. Young foliage upper side: RHS Green 139A. Young foliage under side: RHS Green 139A. Mature foliage upper side: RHS Green 137A. Mature foliage under side: RHS Green 137A.
- *Venation*.—Type: Parallel. Venation coloration: Indistinguished from leaf blade.

Petiole: No petiole present.
Branchlets:
- *Quantity*.—About 6-7.
- *Length*.—About 9 cm.
- *Width*.—About 3 cm.
- *Color*.—RHS Orange-Red 33A.
- *Texture*.—Glabrous.

Bracts:
- *Quantity of bracts on main spike*.—About 12.
- *Arrangement*.—Alternate.
- *Length*.—About 3 cm.
- *Width*.—About 2.4 cm.
- *Overall shape*.—Ovate.
- *Color*.—RHS Orange-Red 33A.
- *Apex*.—Broad acute.
- *Margin*.—Entire.
- *Base*.—Clasping.
- *Texture*.—Glabrous all surfaces.

INFLORESCENCE

General description: 1 flower per floral bract, typical for the genus *Vriesea*; flowering is normally in progression from base to tip of scape.
- *Inflorescence height*.—Approximately 25 cm.
- *Inflorescence width*.—Approximately 12 cm.
- *Shape*.—Bipinnate spike (main spike about 12 cm in length and about 4 cm in width, side spike about 9 cm in length and about 3 cm in width).
- *Color*.—RHS Orange-Red 33A.

Corolla:
- *Form*.—Long and narrow, petals and sepals fused at the base around the ovary.
- *Number*.—About 44 depending on the size of the plant.
- *Size*.—About 3.4 cm long and 0.7 cm in diameter.

Petals:
- *Number*.—3 per flower.
- *Length*.—About 3.5 cm.
- *Width*.—About 0.8 cm.
- *Overall shape*.—Ligulate.
- *Apex shape*.—Obtuse.
- *Base shape*.—Fused.
- *Texture*.—Smooth all surfaces.
- *Margin*.—Entire.
- *Color*.—Upper surface: RHS Yellow 9C. Lower surface: RHS Yellow 9C.

Sepals:

*Number*.—3 per flower.
*Length*.—About 2.5 cm.
*Width*.—About 0.8 cm.
*Overall shape*.—Ligulate.
*Apex shape*.—Acute.
*Base shape*.—Fused.
*Texture*.—Smooth all surfaces.
*Margin*.—Entire.
*Color*.—Closest to RHS Yellow 8A.

REPRODUCTIVE ORGANS

Androecium:

*Stamen*.—Number: 6 per flower. Length: About 3.8 cm. Diameter: About 0.1 cm. Color: RHS Yellow 11C.
*Anther*.—Length: About 0.6 cm. Color: Closest to RHS Yellow 11A.
*Pollen*.—Amount: Not countable. Color: Yellow, too small to qualify R.H.S.

Gynoecium:

*Pistil*.—Number: 1 per flower. Length: About 4.2 cm.
*Stigma*.—Shape: 3-parted. Width: About 0.4 cm. Color: RHS Yellow-Green 145A.
*Style*.—Length: About 3.5 cm. Color: RHS Yellow 11C.
*Ovary*.—Shape: Conical. Length: About 0.5 cm. Diameter: About 0.3 cm. Color: RHS Yellow-Green 150C.

OTHER CHARACTERISTICS

Disease and pest resistance: Neither resistance nor susceptibility to normal diseases and pests of *Vriesea* observed.
Temperature tolerance: Frost tender. Temperatures below 5° C. may damage plants.
Fruit/seed production: No fruits/seeds detected to date.

What is claimed is:

1. A new and distinct cultivar of *Vriesea* plant named 'FLARE' as herein illustrated and described.

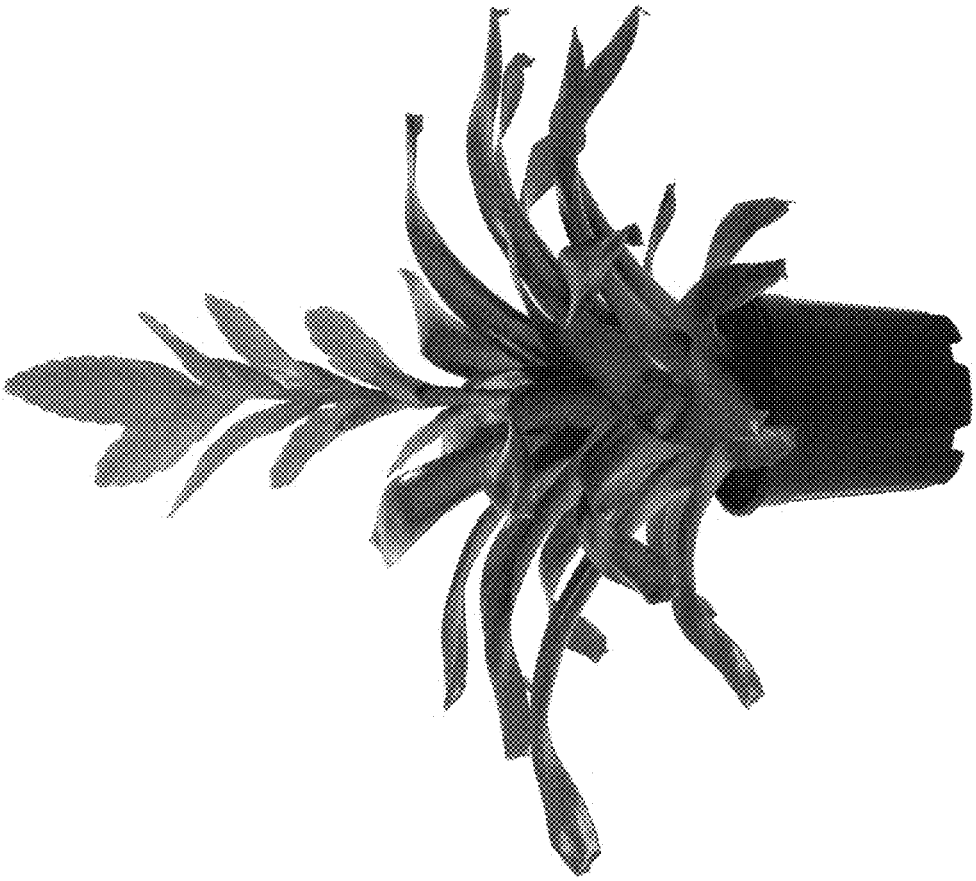

* * * * *